United States Patent
Hedin et al.

(10) Patent No.: US 9,949,690 B2
(45) Date of Patent: Apr. 24, 2018

(54) AUTOMATIC CONFIGURATION SYSTEM FOR AN OPERATOR CONSOLE

(71) Applicant: ABB AB, Västerås (SE)

(72) Inventors: Fredrik Hedin, Brämhult (SE); Pierre Schäring, Sandhult (SE); Pierre Skönnegård, Borås (SE)

(73) Assignee: ABB AB, Västerås (SE)

( * ) Notice: Subject to any disclaimer, the term of this patent is extended or adjusted under 35 U.S.C. 154(b) by 0 days.

(21) Appl. No.: 15/537,674

(22) PCT Filed: Dec. 4, 2015

(86) PCT No.: PCT/EP2015/078636
§ 371 (c)(1),
(2) Date: Jun. 19, 2017

(87) PCT Pub. No.: WO2016/096475
PCT Pub. Date: Jun. 23, 2016

(65) Prior Publication Data
US 2017/0354370 A1    Dec. 14, 2017

(30) Foreign Application Priority Data
Dec. 19, 2014 (SE) ...................... 1430175

(51) Int. Cl.
*G03B 13/14* (2006.01)
*A61B 5/00* (2006.01)
*A61B 5/11* (2006.01)

(52) U.S. Cl.
CPC ............ *A61B 5/681* (2013.01); *A61B 5/1118* (2013.01); *A61B 5/742* (2013.01)

(58) Field of Classification Search
CPC ...... A63F 13/21; A63F 13/211; A63F 13/212; A63F 13/216; A63F 13/235; H04S 7/303;
(Continued)

(56) References Cited

U.S. PATENT DOCUMENTS 6,265,978 B1    7/2001 Atlas
9,751,534 B2 *  9/2017 Fung ...................... B60W 40/08
(Continued)

FOREIGN PATENT DOCUMENTS

WO    2012171032 A2    12/2012

OTHER PUBLICATIONS

Written Opinion of the International Preliminary Examining Authority Application No. PCT/EP2015/078636 dated Nov. 21, 2016 10 Pages.
(Continued)

*Primary Examiner* — Van Trieu
(74) *Attorney, Agent, or Firm* — Whitmyer IP Group LLC

(57) ABSTRACT

An automatic configuration system for an operator console wherein one or more operators control and monitor physical facilities, operations or physically dispersed services. The system includes wearable personal identification devices worn by the operators and a control unit for communicating with the wearable personal identification devices in order to detect the presence of one or more operators within a defined control room area. Each personal identification device includes a sensor unit for monitoring operator data, and is adapted to communicate the operator data to the control unit, which is adapted to configure the operator console based on the operator data.

19 Claims, 3 Drawing Sheets

(58) Field of Classification Search
CPC .. G06F 3/01; A06F 3/011; A06F 3/012; A06F 3/013; A06F 3/014; A06F 3/018; A06F 3/03; A06F 3/16; A06F 3/162; A06F 3/167; A61B 5/681; A61B 5/742; A61B 5/1112; A61B 5/1118; A61B 5/1121; A61B 5/1123

See application file for complete search history.

(56) References Cited

U.S. PATENT DOCUMENTS

| | | |
|---|---|---|
| 2001/0031930 A1 | 10/2001 | Roizen et al. |
| 2004/0027246 A1 | 2/2004 | Aguglia |
| 2009/0055739 A1 | 2/2009 | Murillo et al. |
| 2012/0059581 A1* | 3/2012 | Sambongi ............... G01S 19/34 701/469 |
| 2012/0092172 A1 | 4/2012 | Wong et al. |
| 2013/0049926 A1 | 2/2013 | Hull et al. |
| 2013/0093670 A1 | 4/2013 | Iwai |
| 2014/0072136 A1 | 3/2014 | Tenenbaum et al. |
| 2014/0077955 A1 | 3/2014 | Hollender et al. |
| 2014/0137773 A1 | 5/2014 | Mandel et al. |
| 2014/0207408 A1* | 7/2014 | Yuen ........................ G06K 9/22 702/150 |
| 2017/0085120 A1* | 3/2017 | Leabman ................ H02J 7/042 |
| 2017/0232345 A1* | 8/2017 | Rofougaran .......... A63F 13/573 463/2 |

OTHER PUBLICATIONS

International Preliminary Report on Patentability Application No. PCT/EP2015/078636 dated Feb. 10, 2017 11 Pages.

International Search Report & Written Opinion Application No. PCT/EP2015/078636 Completed Date: Feb. 16, 2016; dated Feb. 25, 2016 14 Pages.

International-Type Search Report Application No. 1430175-8 dated Aug. 25, 2017 4 Pages.

* cited by examiner

AUTOMATIC CONFIGURATION SYSTEM FOR AN OPERATOR CONSOLE

TECHNICAL FIELD

The invention relates to an automatic configuration system for an operator console wherein one or more operators control and monitor physical facilities, operations or physically dispersed services. The system comprises wearable personal identification devices worn by the operators and a control unit for communicating with said wearable personal identification devices in order to detect the presence of said one or more operators within a defined control room area.

BACKGROUND

Control room environments, especially 24/7-type environments, are often static workplaces where little or no physical activity is required for the human operators in control. Such environments can be depressing, unwelcoming and uncomfortable to work in for extended time periods and human operators often suffer from mental fatigue and boredom that may impair their ability to stay alert and proactive at any given time. The importance of improved ergonomics in such control room environments have long been realized by control room designers and much effort is put into this technical field in order to ensure safe operation of the controlled systems or facilities. For example, modern operator consoles can be adjusted in many ways to fit the physical dimensions and personal preferences of an individual human operator. In the past, operator consoles were typically static and once and for all adapted to a theoretical average operator figure based on a "one size fits all" design approach.

Although modern operator consoles may be adjusted to an operator in many ways as described above, the individual settings in present control room systems are generally made manually or by way of separate motor powered or hydraulic activators. Individual settings range from the basic adjustments such as operator desk height, to climate settings and distance to information display monitors. Typically, a problem of inconvenience with current control room systems is that multiple settings must be made separately by the operator in order to achieve an individually adapted work setting for optimal work ergonomics.

SUMMARY

The object of the present invention is to alleviate the problem mentioned above. Hence, the invention discloses an automatic configuration system for an operator console wherein one or more operators control and monitor physical facilities, operations or physically dispersed services. The system comprises wearable personal identification devices worn by the operators and a control unit for communicating with said wearable personal identification devices in order to detect the presence of said one or more operators within a defined control room area. The invention is especially characterized in that each personal identification device includes a sensor unit for monitoring operator data, and is adapted to communicate said operator data to the control unit, which is adapted to configure the operator console based on said operator data.

In a preferred embodiment the operator data includes vital signs and other medical health status parameters. Furthermore, the operator data favourably includes movement pattern data of an operator.

In an advantageous embodiment of the invention, wherein the operator console includes an adjustable height desk, the control unit monitors the movement pattern of an operator and automatically raises the desk to a position corresponding to a standing position of the operator when a predetermined time-period of operator inactivity is detected.

Advantageously, the control unit automatically initiates a change in light intensity, light temperature, air ventilation, sound level or a combination thereof when the sensed operator data indicates a state of drowsiness of the operator.

Furthermore, in a useful embodiment, the control unit monitors the position of an operator relative to the operator console and adapts the information interface depending on the operator's position.

In a further embodiment, the control unit automatically moves the display of prioritized information closer to the sensed position of the operator from a first information display location located at a first distance from the operator to a second information display location located at a second distance from the operator, said first distance exceeding said second distance.

Alternatively, in a case where the control console includes two or more separate information display screens, the control unit automatically moves the display of prioritized information for a dedicated operator from a first information display screen located at a first distance from the operator to a second information display screen located at a second distance from the operator, said first distance exceeding said second distance.

In an advantageous embodiment, the control unit increases the sound volume for alarms and verbal messages with increased distance between the operator and the operator console.

Preferably, each personal identification device is adapted to be programmable with individually adapted operator settings including physical dimension configuration for the operator console. The operator settings are communicated to the control unit upon operator log-in to the operator console and the control unit controls the operator console so as to be configured according to the operator settings. Advantageously, the operator settings further include activation settings enabling or not enabling selective automatic configuration functions.

In one embodiment of the invention, said wearable personal identification and sensor device includes a radio-frequency identification (RFID) tag and may be shaped as a wristband. Accordingly, the control unit preferably includes a radio-frequency identification (RFID) reader. The system may be an Active Reader Passive Tag (ARPT) system or an Active Reader Active Tag (ARAT) system. In an alternative embodiment, the control unit 7 may alternatively communicate with the wearable identification devices by way of so called Near Field Communication technology (NFC) or any other short-range wireless communication technology suitable for the communication.

The invention can be applied in different types of control room environments, such as in electric power plants, ship bridge controls, manufacturing industry and similar environments where a round-the clock alertness must be upheld in order to secure a safe operation.

Further advantages and advantageous features of the invention are disclosed in the following description and in the dependent claims.

BRIEF DESCRIPTION OF THE DRAWINGS

With reference to the appended drawings, below follows a more detailed description of embodiments of the invention cited as examples.

DETAILED DESCRIPTION OF EXAMPLE EMBODIMENTS OF THE INVENTION

Figure 1:
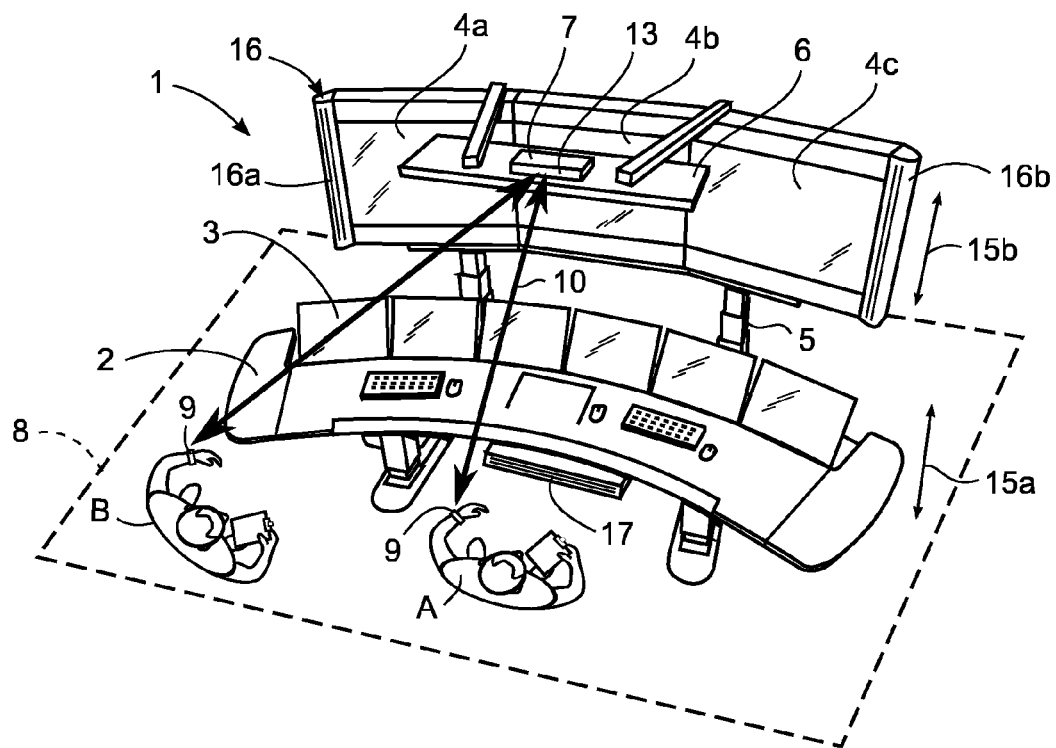
FIG. 1 shows a simplified schematic overview of an operator console equipped with an automatic configuration system according to the present invention.

The invention will now be described with reference to embodiments of the invention and with reference to the appended drawings. With initial reference to FIG. 1, this figure shows a schematic overview of an operator console 1. The operator console 1 in this example is of a larger type designed for two or more operators A, B even though the invention is equally applicable to an operator console of a smaller type intended for one operator only. The operator console 1 includes a desk 2 provided with a multiplicity of information display screens 3, as well as three larger information display screens 4a, 4b, 4c which are supported by a height adjustable support structure 5. A lighting armature 6 is mounted over the desk 2 and a control unit 7 is positioned on the light armature 6 in the shown example. In alternative embodiments, the control unit 7 may be positioned elsewhere on or adjacent to the control console 1.

In FIG. 1, two human operators A, B are shown standing just in front of the desk 2 and within a defined control room area 8 indicated by the dashed square surrounding the operator console 1.

The operators A, B control and monitor physical facilities such as nuclear power plants or physically dispersed services such as emergency rescue operations. The operator console 1 may also be a control bridge of a ship or other large vehicle. According to the invention, the operators A, B are wearing personal identification devices 9 in the shape of wristbands in the shown example. The control unit 7 is adapted to communicate with the personal identification devices 9 when an operator A is within the control room area 8 as indicated by the arrow 10. Hence, the control unit 7 is adapted to detect the presence of the operators A, B within the control room area 8.

Figure 2:
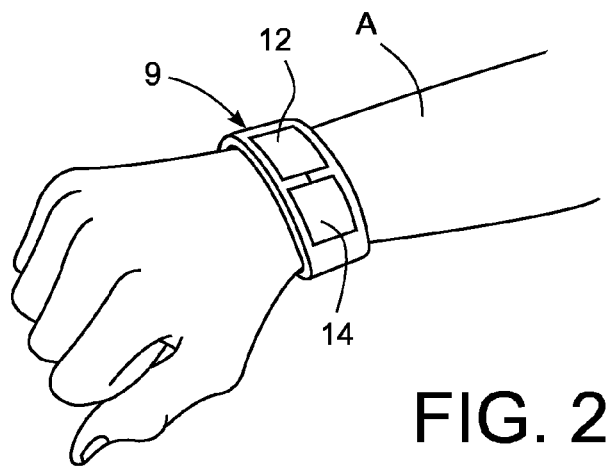
FIG. 2 shows a schematic drawing of an operator's wrist wearing a personal identification device shaped as a wristband and including a radio-frequency identification tag (RFID) tag.

According to the invention, each personal identification device 9 includes a sensor unit 14—as shown in FIG. 2—for monitoring operator data, and is adapted to communicate said operator data to the control unit 7, which is adapted to configure the operator console 1 based on said operator data. The sensor unit 14 includes a non-invasive biometrical sensor for gathering operator data in the form of vital signs and other medical health status parameters. As shown in FIG. 2, the wearable personal identification device 9 includes a radio-frequency identification (RFID) tag 12 and may be shaped as a wristband as shown in the figure, but may alternatively be part of a garment such as a vest (not shown) or be in the form of an ID-card or similar. Accordingly, the control unit 7 preferably includes a radio-frequency identification (RFID) reader 13. The system may be an Active Reader Passive Tag (ARPT) system or an Active Reader Active Tag (ARAT) system. In an alternative embodiment, the control unit 7 may alternatively communicate with the wearable identification devices 9 by way of so called Near Field Communication technology (NFC) or any other short-range wireless communication technology suitable for the communication.

In order to keep the operators A, B alert and to favourably influence their general long term health status the monitored operator data includes movement pattern data of the operators A, B. Hence, the control unit 7 monitors the physical movement pattern of an operator A, B and automatically raises the desk 2 to a position corresponding to a standing position of the operator A, B when a predetermined time-period of operator inactivity is detected. In this case, the desk 2 and the three information display screens 4a, 4b, 4c are raised accordingly as indicated by the arrows 15a, 15b.

The personal identification device 9 is also adapted to send stored information about the operator's A, B individual qualification levels or job positions to the control unit 7. Based on this information, the control unit 7 may selectively display certain information to certain operators depending on their individual job positions or levels of authorization within the system.

Another aspect of the automatic configuration system according to the invention is that the control unit 7 is adapted to automatically initiate a noticeable change in light intensity, light temperature, air ventilation, sound level or a combination thereof when the sensed operator data indicates a state of drowsiness of an operator A, B. In such a case, the control unit 7 sends control commands to the various units needed to be controlled in order to achieve the desired effect of a drowsiness alert. These units include the lighting armature 5, an audio system with loudspeakers 16a, 16b, a micro climate unit 17 all of which are adapted for communication with the control unit 7.

Figure 3A:
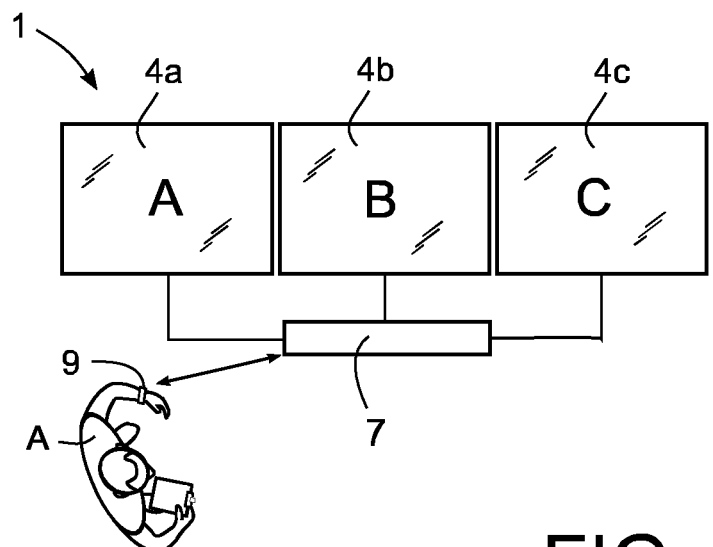
FIG. 3a shows a schematic representation of an operator console with three information display screens and an operator positioned to the left of the console.
Figure 3B:
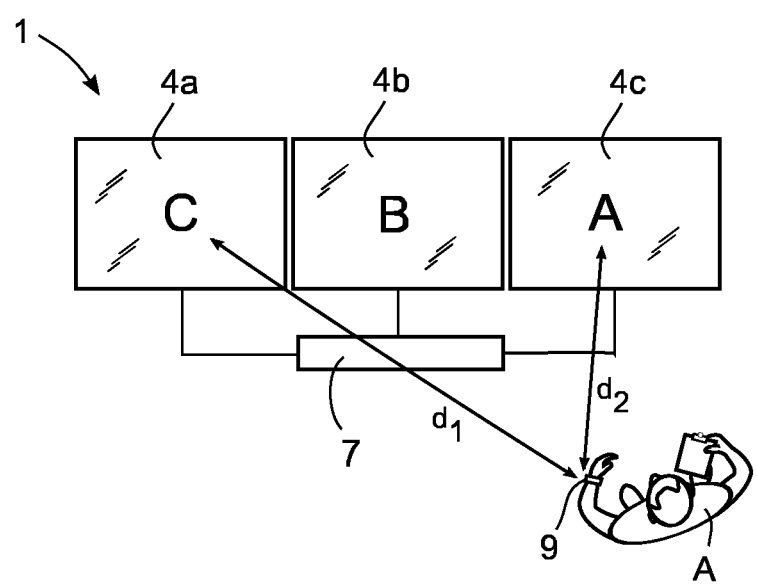
FIG. 3b shows the same operator console as in FIG. 3a but here the operator has moved to the right side of the console, and that the control unit then orders a prioritized information interface to be displayed closer to the operator.

With reference now to FIG. 3a and FIG. 3b, these two figures show a schematic representation of an operator console 1 with three information display screens 4a, 4b, 4c. It should be understood that the operator console 1 may include any number of separate information screens or even a single broad information screen adapted to display separate information display areas corresponding to the separate information screens in the drawings. In FIGS. 3a and 3b only one operator A is shown for the sake of clarity and simplicity. According to the invention, the control unit 7 monitors the position of an operator A relative to the operator console 1 and adapts the information interface depending on the operator's A position. In the figures the information interface is divided into three information displays A, B and C. In FIG. 3a the operator A is in a position closer to display screen 4a than to the two other display screens 4b and 4c. The control unit 7 senses this fact via the wearable personal identification unit 9 worn by operator A and automatically displays the most relevant display interface on the information screen 4a which is located closest to operator A. The inherent relevance of various available display interfaces is stored in the wearable personal identification unit 9 and may depend upon the operator's individual level of training or designated authority within the system as described above.

In FIG. 3b the operator A has now moved to the right side of the operator console 1 from an original position on the left side as shown in FIG. 3a. In this case the control unit 7 senses the new position of the operator A and automatically moves the display of prioritized information—here information display "A" closer to the sensed position of the operator A from a first information display location 4a located at a first distance $d_1$ from the operator A to a second information display location 4c located at a second distance $d_2$ from the operator A, said first distance $d_1$ exceeding said second distance $d_2$. The term display location is here used to further include a wide single display monitor (not shown) on which separate information interfaces A, B, C are displayed. In the shown example, there are three separate information screens 4a, 4b and 4c, although the invention is not limited to such a setup.

Figure 4A:
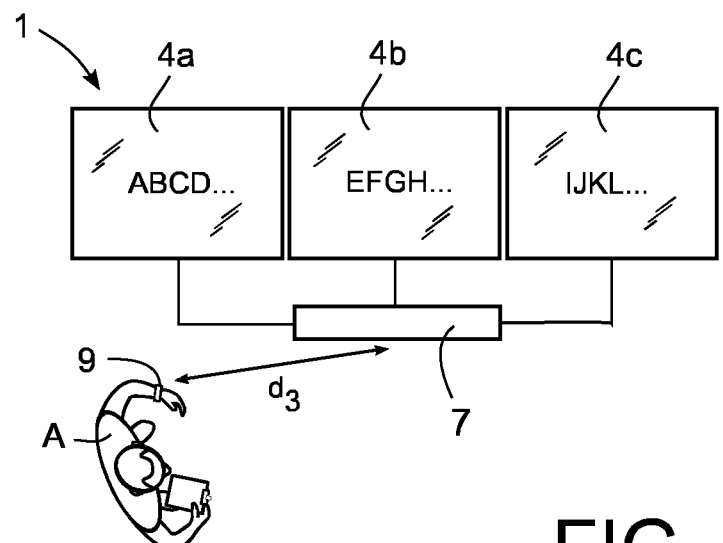
FIG. 4a shows a schematic representation of an operator console with three information display screens and an operator positioned to the left of the console.

In FIG. 4a the same operator console 1 as in the previous FIGS. 3a and 3b is shown displaying three different information contents ABCD, EFGH and IJKL on the three information screens 4a, 4b and 4c respectively. An operator A is positioned to the left of the operator console 1 near display screen 4a at a first, close distance $d_3$ from the control unit 7 and the display screen 4a. The information content is here displayed in a first font size suited for optimal readability at the distance $d_3$.

Figure 4B:
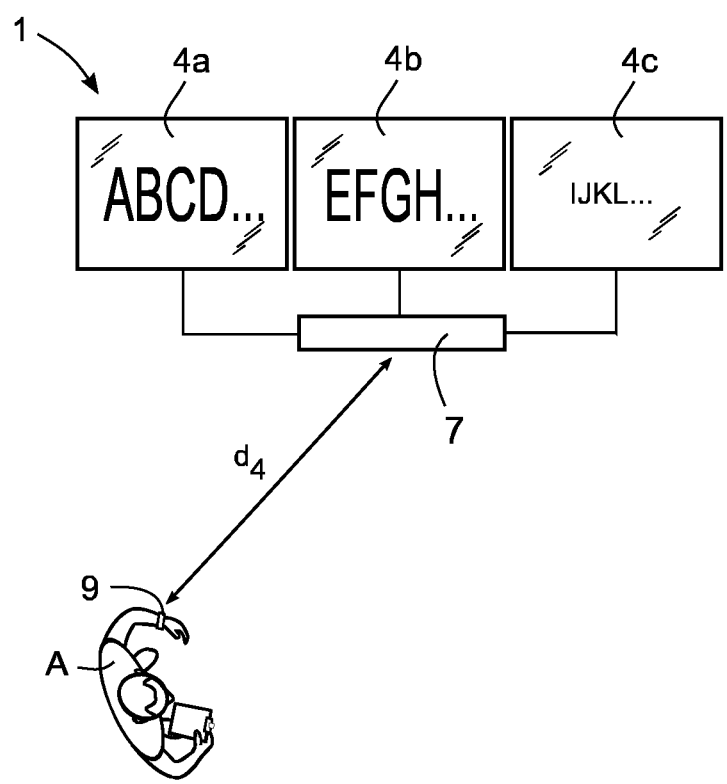
FIG. 4b finally shows a shows the same operator console as in FIG. 4a but here the operator has moved further away from the console, and the control unit then orders a prioritized information interface to be displayed in a larger font size for improved readability by the operator.

In FIG. 4b, the operator A has moved further away from the operator console 1 at a second, greater distance $d_4$ from the control unit 7 and the display screen 4a, relative to the shorter distance $d_3$ in FIG. 4a. The information content on the nearest two information screens 4a, 4b is here displayed in a second, larger font size suited for optimal readability at the distance $d_4$. The information content IJKL at the right information screen 4c maintains its first, smaller font size since it is the least prioritized information content for the specific operator A. Again, this prioritization is made by the control unit 7 on the basis of the operator's individual level of training or designated authority within the system as described above. Furthermore, according to the invention, the control unit 7 increases the sound volume for alarms and verbal messages with increased distance between the operator A and the operator console 1.

According to the invention the personal identification device 9 is adapted to be programmable with individually adapted operator settings including physical dimension configuration for the operator console 1. The operator settings are communicated to the control unit 7 upon operator log-in to the operator console 1, said control unit 7 controlling the operator console 1 so as to be configured according to the operator settings. The operator settings further include activation settings enabling or not enabling selective automatic configuration functions.

It is to be understood that the present invention is not limited to the embodiments described above and illustrated in the drawings and a skilled person will recognize that many changes and modifications may be made within the scope of the appended claims. For example,—as mentioned initially—the control unit 7 may alternatively communicate with the wearable identification devices 9 by way of so called Near Field Communication technology (NFC) or any other short-range wireless communication technology suitable for the communication described above.

The invention claimed is:

1. An automatic configuration system for an operator console wherein one or more operators control and monitor physical facilities, operations or physically dispersed services, said system comprising:

wearable personal identification devices worn by the one or more operators, and a control unit communicating with said wearable personal identification devices in order to detect the presence of said one or more operators within a defined control room area, wherein each personal identification device includes a sensor unit for monitoring operator data, and is adapted to communicate said operator data to the control unit, wherein the control unit is adapted to:
configure the operator console based on said operator data,
monitor a position of an operator relative to the operator console, and
configure an information interface depending on the position by automatically moving the display of prioritized information closer to the sensed position of said operator from a first information display location located at a first distance from the operator to a second information display location located at a second distance from the operator, the first distance exceeding the second distance.

2. The automatic configuration system for an operator console according to claim 1, wherein said operator data includes vital signs and other medical health status parameters.

3. The automatic configuration system for an operator console according to claim 2, wherein the control unit automatically initiates a change in light intensity, light temperature, air ventilation, sound level or a combination thereof when the operator data indicates a state of drowsiness of the operator.

4. The automatic configuration system for an operator console according to claim 1, wherein said operator data includes movement pattern data of the operator.

5. The automatic configuration system for an operator console according to claim 4, wherein the operator console includes an adjustable height desk, wherein said control unit monitors the movement pattern of the operator and automatically raises the desk to a position corresponding to a standing position of the operator when a predetermined time-period of operator inactivity is detected.

6. The automatic configuration system for an operator console according to claim 1, wherein the control console includes two or more separate information display screens, wherein the control unit automatically moves the display of prioritized information for a dedicated operator from a first information display screen located at the first distance from the operator to a second information display screen located at the second distance from the operator, said first distance exceeding said second distance.

7. The automatic configuration system for an operator console according to claim 6, wherein said control unit increases a sound volume for alarms and verbal messages with increased distance between the operator and the operator console.

8. The automatic configuration system for an operator console according to claim 6, wherein each personal identification device is configured to be programmable with individually adapted operator settings including physical dimension configuration for the operator console, said operator settings being communicated to the control unit upon operator log-in to the operator console, said control unit controlling the operator console so as to be configured according to the operator settings.

9. The automatic configuration system for an operator console according to claim 6, wherein at least one of said wearable personal identification devices includes a radio-frequency identification tag.

10. The automatic configuration system for an operator console according to claim 6, wherein said control unit includes a radio-frequency identification reader.

11. The automatic configuration system for an operator console according to claim 1, wherein said control unit increases a sound volume for alarms and verbal messages with increased distance between the operator and the operator console.

12. The automatic configuration system for an operator console according to claim 1, wherein each personal identification device is configured to be programmable with individually adapted operator settings including physical dimension configuration for the operator console, said operator settings being communicated to the control unit upon operator log-in to the operator console, said control unit controlling the operator console so as to be configured according to the operator settings.

13. The automatic configuration system for an operator console according to claim 12, wherein said operator settings further include activation settings enabling or disabling selective automatic configuration functions.

14. The automatic configuration system for an operator console according to claim 1, wherein at least one of said wearable personal identification devices includes a radio-frequency identification tag.

15. The automatic configuration system for an operator console according to claim 14, wherein at least one of the wearable personal identification devices is shaped as a wristband.

16. The automatic configuration system for an operator console according to claim 14, wherein the system is an Active Reader Passive Tag system.

17. The automatic configuration system for an operator console according to claim 14, wherein the system is an Active Reader Active Tag system.

18. The automatic configuration system for an operator console according to claim 1, wherein said control unit includes a radio-frequency identification reader.

19. An automatic configuration system for an operator console wherein one or more operators control and monitor physical facilities, operations or physically dispersed services, said system comprising:
   wearable personal identification devices worn by the one or more operators, and
   a control unit communicating with said wearable personal identification devices in order to detect the presence of said one or more operators within a defined control room area,
   wherein each personal identification device includes a sensor unit for monitoring operator data and is adapted to communicate said operator data to the control unit, said operator data includes movement pattern data of the operator,
   wherein the control unit is adapted to configure the operator console based on said operator data, and
   wherein the operator console includes an adjustable height desk, said control unit monitors the movement pattern of the operator and automatically raises the desk to a position corresponding to a standing position of the operator when a predetermined time-period of operator inactivity is detected.

* * * * *